United States Patent [19]

Idenden

[11] 4,395,310

[45] Jul. 26, 1983

[54] FRACTIONATION SYSTEM

[75] Inventor: John E. Idenden, Belleville, N.J.

[73] Assignee: Exxon Research and Engineering Co., Florham Park, N.J.

[21] Appl. No.: 283,231

[22] Filed: Jul. 14, 1981

[51] Int. Cl.³ .............................................. B01D 3/42
[52] U.S. Cl. .......................................... 203/2; 203/24; 203/26; 203/DIG. 4; 203/DIG. 8; 203/DIG. 18; 208/DIG. 1
[58] Field of Search .................... 203/1, 2, 24, 26, 21, 203/23, 25, DIG. 18, DIG. 4, DIG. 8; 585/800; 202/160; 208/DIG. 1; 196/132; 62/26, 30, 21, 37

[56] References Cited

U.S. PATENT DOCUMENTS

| | | | |
|---|---|---|---|
| 2,509,136 | 5/1950 | Cornell | 202/40 |
| 2,577,701 | 12/1951 | Deming et al. | 62/175.5 |
| 3,225,550 | 12/1965 | Kelly et al. | 62/26 |
| 4,023,946 | 5/1977 | Schwartzman | 62/40 |
| 4,057,407 | 11/1977 | Bigi | 62/30 |
| 4,137,129 | 1/1979 | Bjorklund | 203/26 |

Primary Examiner—Frank Sever
Attorney, Agent, or Firm—Edward H. Mazer

[57] ABSTRACT

A method for decreasing the external energy input to a fractionation system is disclosed. The method utilizes a compression zone communicating with either the overhead fraction or the bottoms fraction from a fractionation zone. The method is directed at regulating the rate of energy addition and/or removal to the fractionation zone by at least one of the fractions returned to the fractionation zone to maintain the separated fractions within the desired limits.

4 Claims, 2 Drawing Figures

FRACTIONATION SYSTEM

BACKGROUND OF THE INVENTION

This invention is directed at a process for separating a feed into a distillate and a bottoms which utilizes less energy than previous designs. More specifically, the subject design is directed at an improved fractionation system utilizing a compression means to reduce the energy requirements of the system as compared with other fractionation systems.

The fractionation of a feed into a distillate and a bottoms is well-known in the art. The fractionation system normally includes a fractionation or distillation zone, a reboiler for reheating the bottoms and returning the bottoms to the distillation zone and a condenser for condensing the distillate from the distillation zone. Typically the reheated bottoms is returned to the column for at least partial vaporization, and the unvaporized portion is removed. The distillate normally is at least partially condensed. A fraction is removed from the system, while the remainder is returned to the distillation zone as reflux. This intermixing of liquid and vapor is necessary for good separation of the feed into the desired distillate and bottoms. Fractionation systems frequently consume large amounts of energy for reboiling the bottoms and large amounts of cooling water for cooling and condensing the distillate. With the increasing cost of energy, efforts are being made to utilize waste heat sources for supplying energy to fractionation systems. Where waste heat sources are not available, other methods of decreasing the net energy consumption of a fractionation system are being considered. It is known in the art to utilize compressors in conjunction with distillation systems. U.S. Pat. No. 2,577,701 utilizes compressors for increasing the pressure of several streams in a fractionation system. U.S. Pat. No. 2,509,136 discloses a system in which the distillate from a fractionation column is compressed and passed in indirect contact with the bottoms to transfer heat to the bottoms. The distillate then is split into two streams, a reflux stream returned to the first column and a second stream which serves as a feed to a second column. A flow controller is inserted to assure constant reflux to the first column. The speed of the turbine is varied to vary the distillate feed rate to the second tower as the composition changes. This results in variation in the reboiling rate and hence a variation in the fractionation efficiency. U.S. Pat. No. 4,023,946 discloses an elaborate fractionation system in which a closed fluid system may be alternatively compressed and expanded to provide reboiling and condensation for the fractionation system. This system does not provide means for maintaining the distillate quality in a relatively simple, reliable manner. U.S. Pat. No. 4,137,129 describes a process in which the bottoms liquid stream from the fractionation column is flashed to cool the liquid which is then used to condense the distillate from the column. The flashed vapor from the bottoms is compressed and used to reboil the contents of the column. This system also does not provide means for regulating the distillate characteristics in a simple, energy efficient manner.

One method for increasing the heat available in the distillate for reboiling the bottoms utilizing compressors is to provide additional preheat to the overheads from the tower to the compressor. There are, however, practical limitations to the addition of preheat to the overheads subsequently passed through a compressor. One limit is the maximum allowable discharge temperature for the compressor and another is the temperature of the available heat source. If the heat source is at a very high temperature it may be more advantageous to use the heat directly to reboil the tower.

Accordingly it is desirable to provide a process which is energy efficient and reliable and applicable where there is no source available at a very high temperature.

It is also desirable to provide a process which permits relatively close regulation of the fractionation operation without the use of elaborate control systems.

It is further desirable to provide a process which permits a heat source to be utilized in a process having a compressor without exceeding the maximum allowable working pressure of the compressor.

The subject invention, although useful when there is a heat source available at a very high temperature, is more particularly applicable where the available heat source is at a relatively low temperature and where the difference in boiling points of the distillate and bottoms is relatively small.

SUMMARY OF THE INVENTION

The subject invention is directed at a method for reducing the energy input to a fractionation system of the type comprising:

A. a fractionation zone communicating with a feed source, the fractionation zone adapted to separate the feed into an overhead fraction and a bottoms fraction;

B. a reboiler zone communicating with the fractionation zone whereby at least a portion of the bottoms fraction from the fractionation zone passes into the reboiler zone for reheating prior to return to the fractionation zone, and whereby at least a portion of the overhead fraction passes through the reboiler zone to reheat the bottoms fraction, at least a portion of the overhead fraction thereafter returned to the fractionation zone; and C. a compression zone communicating with one of the fractions whereby the improvement comprises regulating the rate of energy addition to and/or removal from the fractionation zone by at least one of the fractions returned to the fractionation zone to maintain the separated fractions within the desired limits.

The compression zone may communicate with either the bottoms fraction or the overhead fraction. Where the condensation of the overhead fraction does not impart sufficient energy to the bottoms to effectuate the desired separation, additional energy may be added. When the compression zone communicates with the overhead fraction, additional energy may be imparted by undercooling the overhead fraction returned to the distillation zone. Where the bottoms fraction communicates with the compression zone, the overhead fraction returned to the distillation zone preferably is heated with an external heat source prior to being returned to the distillation zone.

DETAILED DESCRIPTION OF THE INVENTION

The subject invention is directed at a method for utilizing the latent heat in the distillation column overheads for reboiling the bottoms recirculated to the distillation column while monitoring and controlling the distillate characteristics. One method for increasing the heat available in the distillate for reboiling the bottoms utilizing compressors is to provide additional preheat to the overheads from the tower to the compressor. There are, however, practical limitations to the addition of preheat to the overheads subsequently passed through a compressor. One limit is the maximum allowable discharge temperature for the compressor and another is the temperature of the available heat source. If the heat source is at a very high temperature it may be advantageous to use the heat directly to reboil the tower. The subject invention, although useful when there is a heat source available at a very high temperature, is more particularly applicable where the available heat source is at a relatively low temperature. The subject invention is directed, in part, at increasing the tower overheads by undercooling the overheads returned to the column. In the figures described hereinafter alternate methods for practicing the subject invention are shown. In these figures all pumps, piping, instrumentation and similar items not essential to an understanding of this invention have been omitted for clarity.

Figure 1:
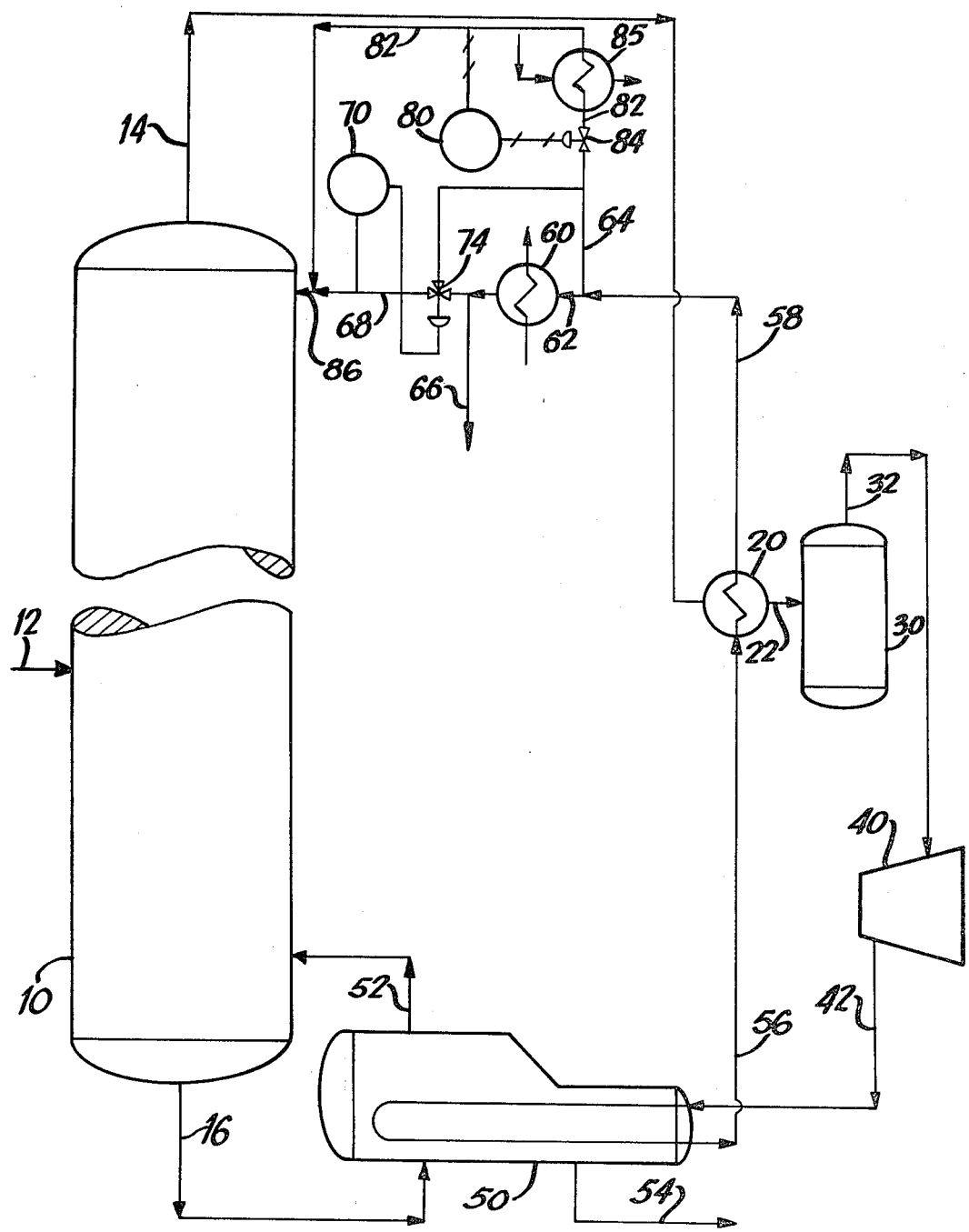
FIG. 1 is a simplified schematic flowsheet of one method for practicing the subject invention.

Referring to FIG. 1, one method for practicing the subject invention is shown. In this figure a feed stream 12 to be fractionated is passed into a fractionation zone, such as distillation or fractionation column 10. In column 10 the feed is separated into a relatively low boiling fraction which exits the top of the column through line 14 and a less volatile bottoms fraction which is removed from the base of the column through line 16. In the embodiment shown, the distillate in line 14, frequently referred to as overheads, passes through heat exchanger 20 to raise the temperature of the overheads and passes through line 22 into knock-out pot 30, where condensibles are removed. The overheads then pass from knock-out pot 30 through line 32 into a compression zone, such as compressor 40, where the pressure of the overheads stream is increased. The mechanical energy associated with compressing the overheads also operates to raise the temperature of the overheads exiting from compressor 40 through line 42. The compressed overheads pass through a reboiling zone, such as reboiler or heat exchanger 50, where the overheads transfer heat to the bottoms entering the reboiler through line 16. In a typical operation, the compressed overheads in line 42 enter reboiler 50 as a vapor at a higher temperature than the bottoms which enter reboiler 50 as a liquid through line 16. The condensation of the overheads operates to vaporize the bottoms which exit reboiler 50 through line 52. Depending upon the downstream temperature requirement for the bottoms product, a bottoms stream may be removed from the process from different locations relative to reboiler 50. In the process shown, bottoms product is removed through line 54 after passing through reboiler 50. The condensed overheads pass from reboiler 50 through line 56 into heat exchanger 20 where additional heat is transferred to the overheads from line 14 as previously described. The condensed overheads exiting heat exchanger 20 pass through line 58 where the stream may be split into a stream 62 which passes through heat exchanger 60 for further cooling and a by-pass stream 64, which does not pass through heat exchanger 60. The overheads exiting the process frequently must be cooled. Accordingly, the overheads exiting the process are shown passing through heat exchanger 60 prior to being removed from the system through line 66. Temperature controller 70 monitors the temperature of the fluid in line 68 and adjusts control valve 74 to regulate the amount of fluid permitted to by-pass heat exchanger 60.

The pressure in line 64 will be higher than in line 68. Thus, a fraction of the overheads in line 64 will flash upon entry into line 68, thereby generating additional vapor for circulation through compression zone 40 and reboiler zone 50. This additional vapor, or overflash, which is generated by undercooling at least a portion of the overheads returned to the fractionation zone, may be used to increase the overheads rate, and, in turn, the energy transfer rate to the bottoms fraction in reboiler zone 50.

If additional heat is required for the process this can be provided, among many ways, by adding heat to the reboiler or to the overheads returned to column 10. It may be most efficient to add heat to the bottoms streams 16 or 52. However, since the overheads being returned to column 10 through line 64 usually are at a lower temperature than the bottoms stream, a heating fluid at a lower temperature than the bottoms frequently can be used to heat stream 64. In this figure a second temperature controller 80 sensing the temperature in line 82 regulates control valve 84 to adjust the flow rate of overheads through 82 and heat exchanger 85. The overheads from lines 82 and 68 join to form line 86 which enters column 10 near the top. A portion of this overhead stream may flash upon entering the column to provide additional overhead vapor which ultimately is utilized to heat bottoms stream 16.

Figure 2:
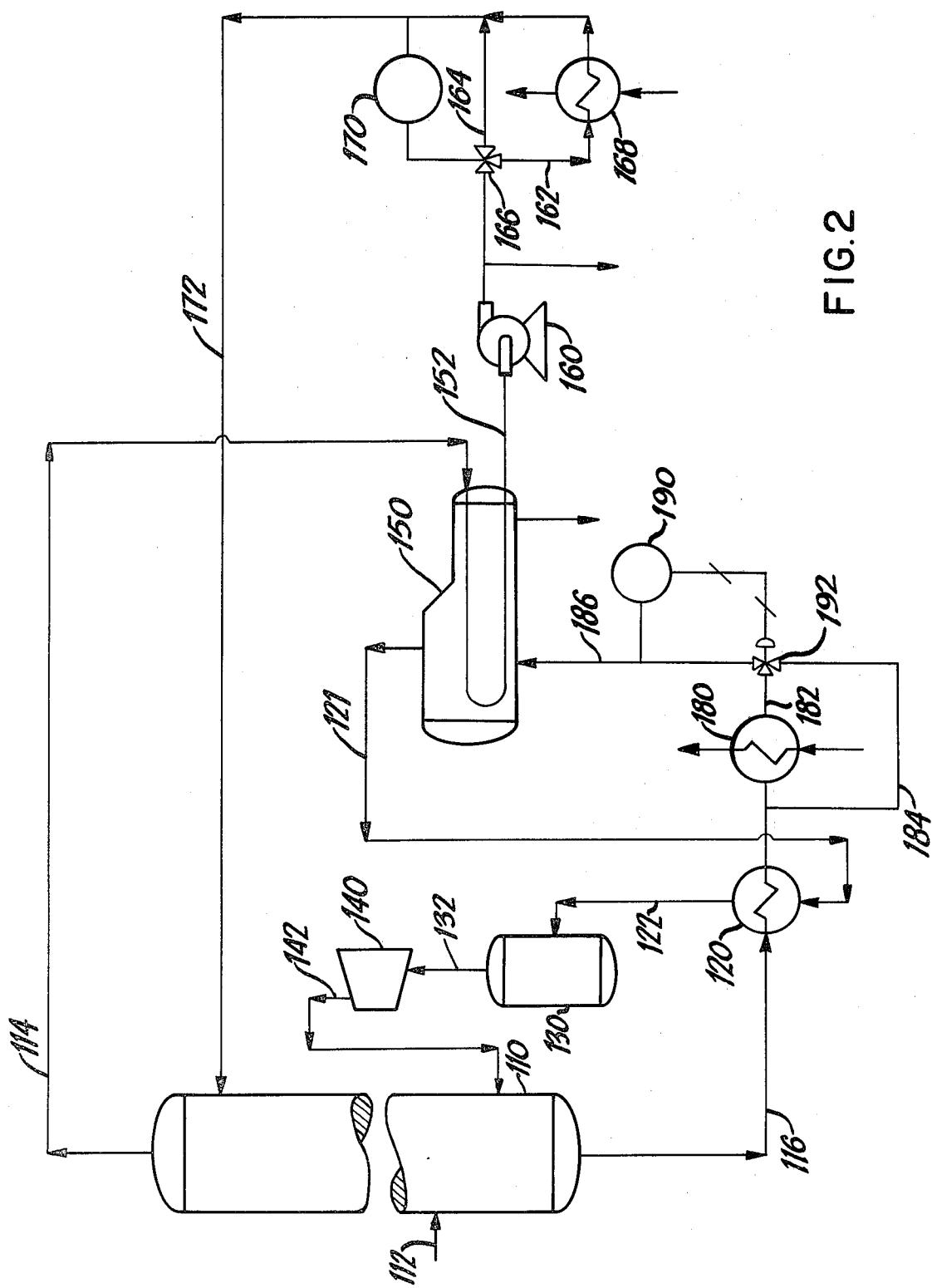
FIG. 2 is a simplified schematic flowsheet of an alternate method for practicing the subject invention.

Referring to FIG. 2 an alternate, energy efficient process for separating a more volatile fraction from a less volatile fraction is shown. In this process the compressor communicates with the bottoms fraction being returned to the column rather than with the overhead fraction. In this process an inlet feed stream 112 to fractionation column 110 is separated in the column into an overheads fraction 114 and a bottoms fraction 116. The overheads pass into reboiler 150 for indirect heat transfer to the bottoms. The overheads typically will be condensed in reboiler 150 with the overhead condensate exiting through line 152. Pump 160 operates to transfer the overhead condensate through lines 162, 164 and 172. The relative amount of condensate flowing through lines 162 and 164 is governed by temperature controller 170 which operates control valve 166. In this figure, all flow through line 162 passes through heat exchanger 168 which may be used to increase or decrease the temperature of the overhead condensate. The bottoms fraction passes from line 116 through heat exchanger 120 which cools the bottoms prior to entry into reboiler 150 by heat exchange with bottoms in line 121. If an excess quantity of heat, i.e., an amount greater than that required for operation of the column is supplied by the condensation of the overhead fraction, the bottoms stream to the reboiler preferably is cooled in optional heat exchanger 180 to eliminate excess work by compressor 140. Temperature controller 190 controls valve 192 to adjust the relative flow through lines 182 and 184 to thereby regulate the cooling in the bottoms. Lines 182 and 184 join to form line 186 which enters reboiler 150.

The inlet to compressor 140 operates to reduce the absolute pressure of the bottoms in reboiler 150 allowing the bottoms to be vaporized by the condensation of the overhead fraction in the reboiler. The vaporized bottoms pass from reboiler 150 through line 121 to heat exchanger 120 where additional energy is imparted to the vapor fraction by indirect contact to decrease the amount of condensables present. The bottoms then pass through line 122 into knock-out pot 130 where condensed material in the bottoms is removed. The bottoms vapor then passes through line 132 into compressor 140 where it is compressed and further heated by the mechanical energy imparted. The bottoms are discharged through line 142 into column 110.

The decision on whether to use the method of FIG. 1 or the method of FIG. 2 will be dependent, in part on the process conditions of the particular system. For example where the process conditions using the method of FIG. 1 might raise the temperature or pressure to undesirably high levels, the method of FIG. 2 might be utilized.

The use of a compression zone to recover energy from the overhead fraction for use in vaporizing a portion of the bottoms fraction is particularly applicable where the difference in boiling points of the overhead and bottoms fractions is relatively small, such as less than about 35° C. Above this temperature, the capital and operating costs associated with operating a compression zone for transferring energy from the overhead fraction to the bottoms fraction may outweigh the energy savings.

The following examples will illustrate the utility of the present invention in reducing the energy requirements as compared with previous fractionation systems.

In the following examples, the energy requirements of $C_4$ splitter distillation zones for the separation of n-butane from iso-butane are compared. The distillation zones had a feed rate of 93,000 #/hr which was separated into 70,000 #/hr of iso-butane overheads and 23,000 #/hr of n-butane bottoms. In the comparative case shown, with no compression zone, the overhead fraction was condensed using an external cooling source and the bottoms fraction was heated using an external heat source. Table I shows the energy reduction calculated when using the embodiment of FIG. 1. Table II illustrates the energy reduction calculated when the embodiment of FIG. 2 is utilized.

In the fractionation systems described herein all the equipment utilized may be of conventional designs, well-know in the art. The fractionation tower may be, for example, a packed tower or a tower having trays therein which will provide acceptable vapor-liquid contacting within the operating parameters of the system. The heat exchangers and reboilers usually will be shell-and-tube heat exchangers, although other methods of indirect heat transfer also may prove satisfactory. The compressor frequently is of the centrifugal type although other designs such as positive displacement and axial compressors also may prove satisfactory.

TABLE I

|  | NO COMPRESSION ZONE | COMPRESSION ZONE COMMUNICATING WITH OVERHEAD FRACTION |
|---|---|---|
| Reboiler Heat Required, MBtu/hr | 47.8 | 47.8 |
| Heat Source | External | Condensation of Overhead |
| Compressor Work Heat Equivalent, MBtu/hr | — | 13.7 |
| Condensation Heat Available, MBtu/hr with Undercooling Overhead Fraction, MBtu/hr | 46.0 | 46.0 |
|  | — | 47.8 |
| External Heat Equivalent Required, MBtu/hr | 47.8 | 13.7 |
| Net Energy Savings Utilizing Compression Zone, MBTu/hr | — | 34.1 |
| Reflux Pump Required | Yes | No |

TABLE II

|  | NO COMPRESSION ZONE | COMPRESSION ZONE COMMUNICATING WITH BOTTOMS FRACTION |
|---|---|---|
| Reboiler Heat Required, MBtu/hr | 53.1 | 53.1 |
| Heat Source | External | Condensation of Overhead |
| Compressor Work Heat Equivalent, MBtu/hr | — | 16.4 |
| Condensation Heat Available, MBtu/hr | 46.0 | 46.0 |
| with Reheat of Overheads, MBtu/hr | — | 47.7 |
| Net Energy Savings Utilizing Compression Zone, MBtu/hr | — | 35.0 |
| Total External Heat Equivalent Required For Compression Zone Operation and for Reheat of Overheads, MBtu/hr | 53.1 | 18.1 |
| Reflux Pump Required | Yes | Yes |

What is claimed is:

1. A method for reducing the energy input to a fractionation system comprising a fractionation zone, a reboiler zone communicating with the fractionation zone, and a compression zone communicating with the fractionation zone and the reboiler zone, said method comprising:
   A. introducing a hydrocarbon feed into the fractionation zone, the fractionation zone adapted to separate the feed into an overhead fraction and a bottoms fraction;
   B. passing at least a portion of the bottoms fraction from the fractionation zone through a reboiler zone for reheating prior to returning bottoms fraction to the fractionation zone;
   C. passing overhead fraction through a compression zone wherein the overhead fraction is compressed;
   D. passing substantially all the overhead fraction from the compression zone through the reboiler zone, the compressed overhead fraction transferring heat to the bottoms fraction;
E. returning an overhead fraction consisting of a liquid phase quantity and a vapor phase quantity to the fractionation zone;
F. monitoring the composition of at least one of the fractions separated in the fractionation zone; and,
G. regulating the rate of said liquid phase quantity of the overhead fraction returned to the fractionation zone sufficient to thereby reduce the energy input to the fractionation system as compared to a fractionation system having no compression zone.

2. The method of claim 1 wherein the overhead fraction from the fractionation zone is preheated prior to entering the compression zone by the overhead fraction from the reboiler zone.

3. The method of claim 2 wherein at least a portion of the overhead fraction returned to the fractionation zone is further heated by an external heat source.

4. The method of claim 2 wherein a portion of the overhead fraction from the reboiler zone is removed after preheating the overhead fraction from the fractionation zone.

* * * * *